United States Patent
Sherman

(10) Patent No.: US 6,485,744 B1
(45) Date of Patent: Nov. 26, 2002

(54) STABILIZED CEFUROXIME AXETIL

(75) Inventor: Bernard Charles Sherman, 50 Old Colony Road, Willowdale, Ontario (CA), M2L 2K1

(73) Assignee: Bernard Charles Sherman, Willowdale (CA)

(*) Notice: Subject to any disclaimer, the term of this patent is extended or adjusted under 35 U.S.C. 154(b) by 0 days.

(21) Appl. No.: 09/621,676

(22) Filed: Jul. 24, 2000

(30) Foreign Application Priority Data

Jul. 29, 1999 (CA) ............................................... 2280925

(51) Int. Cl.[7] .......................... A61K 9/20; A61K 9/00; A61K 9/14
(52) U.S. Cl. ..................... 424/464; 424/400; 424/465; 424/489
(58) Field of Search .............................. 424/400, 464, 424/468, 489

(56) References Cited

U.S. PATENT DOCUMENTS

| 4,267,320 | A |   | 5/1981  | Gregson et al. ............... 544/22 |
| 4,562,181 | A |   | 12/1985 | Crisp et al. .................. 514/202 |
| 4,820,833 | A |   | 4/1989  | Crisp et al. |
| 4,895,727 | A | * | 1/1990  | Allen ......................... 424/642 |
| 4,897,270 | A |   | 1/1990  | Deutsch et al. |
| 4,968,508 | A | * | 11/1990 | Oren et al. .................. 424/468 |
| 5,063,224 | A | * | 11/1991 | Mosher et al. ............... 514/202 |
| 5,776,495 | A |   | 7/1998  | Duclos et al. ............... 424/455 |
| 6,207,718 | B1| * | 3/2001  | Papadimitriou ........... 514/772.3 |

FOREIGN PATENT DOCUMENTS

CA         2209868        2/1999

* cited by examiner

Primary Examiner—Thurman K. Page
Assistant Examiner—Robert M. Joynes
(74) Attorney, Agent, or Firm—Neil H. Hughes; Ivor M. Hughes; Marcelo K. Sarkis

(57) ABSTRACT

Solid pharmaceutical compositions comprising cefuroxime axetil as active ingredient and a zinc salt as stabilizer.

17 Claims, No Drawings

STABILIZED CEFUROXIME AXETIL

BACKGROUND

Cefuroxime axetil is an antibiotic effective against a wide spectrum of microorganisms when administered orally.

Solid compositions for oral administration comprising cefuroxime axetil are presently available commercially in the form of tablets, and as powders for oral suspension.

There are substantial difficulties in the production of satisfactory solid compositions comprising cefuroxime axetil.

One problem is that it is difficult to make compositions for oral administration which provide high bioavailability; that is to say, that are well absorbed from the gastrointestinal tract into systemic circulation. In particular, if the cefuroxime axetil is in crystalline form, it exhibits poor water solubility and hence poor absorption.

U.S. Pat. No. 4,820,833 discloses that absorption can be improved by using cefuroxime axetil in pure amorphous form instead of crystalline form.

U.S. Pat. No. 4,897,270 further discloses that absorption from film coated tablets can be improved by formulating the tablets such that, when a tablet is ingested, the film coating ruptures rapidly in the gastrointestinal fluid, and the core then disintegrates immediately.

Canadian patent no. 2209868 discloses that, instead of using cefuroxime axetil in pure amorphous form, excellent dissolution and absorption can also be achieved by using cefuroxime axetil in the form of a co-precipitate of cefuroxime axetil and a water-soluble excipient.

A second problem in formulating satisfactory solid compositions comprising cefuroxime axetil is that cefuroxime axetil is relatively unstable in the presence of many common excipients (i.e. inactive ingredients) used to make solid pharmaceutical compositions.

The object of the present invention is to provide a means of stabilizing cefuroxime axetil, so as to reduce the rate of degradation of cefuroxime axetil in solid pharmaceutical compositions.

DESCRIPTION OF THE INVENTION

It has been surprisingly found that cefuroxime axetil can be stabilized by admixture with a zinc salt, preferably zinc chloride.

Compositions of the present invention will thus be solid pharmaceutical compositions comprising cefuroxime axetil as active ingredient and a zinc salt as stabilizer.

The amount of zinc salt in the composition will preferably be from about 0.1 to about 4 parts per 100 parts cefuroxime axetil by weight; more preferably from about 0.2 to about 2 parts per hundred parts cefuroxime axetil by weight; and most preferably about one part per hundred parts cefuroxime axetil by weight.

In order to enable maximum bioavailability, the cefuroxime axetil in the composition will preferably be in pure amorphous form or in the form of a co-precipitate with a water-soluble diluent.

The zinc salt may be added to the composition at any point in the process of production of the composition.

However, when the cefuroxime axetil is used in pure amorphous form or in the form of a co-precipitate, the zinc salt will preferably be added, in the process of making the pure amorphous cefuroxime axetil or the co-precipitate, in order to get a more intimate mixture of the zinc salt with the cefuroxime axetil.

In the case of pure amorphous cefuroxime axetil, the process of manufacture will preferably be to dissolve the zinc salt along with the cefuroxime axetil in suitable solvent and then evaporate the solvent, preferably by spray-drying, in order to produce amorphous material comprising cefuroxime axetil and a small amount of zinc salt intimately mixed therein.

Similarly, in the case of a co-precipitate, the process will preferably be to dissolve the cefuroxime axetil, water-soluble diluent, and zinc salt together in suitable solvent and evaporate the solvent, again preferably by spray-drying to produce an amorphous co-precipitate comprising the cefuroxime axetil, water-soluble diluent, and zinc salt.

The amorphous material comprising cefuroxime axetil and zinc salt, or cefuroxime axetil, water-soluble diluent, and zinc salt, will then be further processed into the final solid composition which, as aforesaid, may be a tablet, or a powder or granules for oral suspension; that is to say, powder or granules to which water is to be added to provide a suspension for pediatric use.

The invention will be further illustrated by the following examples, which are intended to be illustrative but not limiting of the scope of the invention.

Solutions were made by dissolving cefuroxime axetil, sorbitol and zinc chloride in acetone and water in the proportions shown.

|  | Example #1 | Example #2 | Example #3 | Example #4 |
| --- | --- | --- | --- | --- |
| Cefuroxime axetil | 90. | 90. | 90. | 90. |
| Sorbitol | 10. | 9.6 | 9.0 | 8.0 |
| zinc chloride | 0 | 0.4 | 1.0 | 2.0 |
| Acetone | 400 | 400 | 400 | 400 |
| Water | 100 | 100 | 100 | 100 |
|  | 600 | 600 | 600 | 600 |

Each of the solutions of examples 1 to 4 was then spray-dried to produce an amorphous co-precipitate comprising 90% cefuroxime axetil by weight.

On a dried basis, the percentage of zinc chloride by weight was nil in example 1, 0.4% in example 2, 1% in example 3, and 2% in example 4.

In each case, the spray-dried co-precipitate was further processed by mixing the co-precipitate with other ingredients in the following proportions.

| Co-precipitate | 694. |
| --- | --- |
| Crospovidone | 358. |
| Zinc stearate | 8. |
|  | 1060. |

In each case, the mixture was then compressed into tablets of weight 1060 mg per tablet. Each tablet thus contained 694 mg of co-precipitate, which in turn comprised 90%×694 mg or 624.2 mg of cefuroxime axetil, which is equivalent to about 500 mg of cefuroxime. The crospovidone is a disintegrant, and the zinc stearate is a lubricant to prevent sticking to the tooling in the tabletting process.

The tablets of each of these examples were then subjected to an accelerated stability trial, in which samples were stored at 60° C. for 7 days. The samples were then tested to determine the amount by which related impurities (i.e. degradation products) increased during the 7 days at 60° C. The results were as follows:

|  | Example #1 | Example #2 | Example #3 | Example #4 |
|---|---|---|---|---|
| % zinc chloride in co-precipitate | 0% | 0.4% | 1% | 2% |
| increase in RC1 | 0.29% | 0.12% | 0.06% | 0.05% |
| increase in other impurities | 0.09% | 0.11% | 0.11% | 0.17% |
| increase in total impurities | 0.38% | 0.23% | 0.17% | 0.21% |

RC1 is delta-2-cefuroxime axetil.

It can be seen that the increase in RC1 upon storage at 60° C. for 7 days was 0.29% for the tablets of example 1, which contained no zinc chloride. The increase was less for examples 2, 3, and 4, but not significantly less for example 4 than for example 3.

On the other hand, the increase in other impurities was more rapid as the level of zinc chloride is increased. The increase in total impurities was the least for example 3, which had 1% zinc chloride in the co-precipitate.

Since the co-precipitate of example 3 comprised 90% cefuroxime axetil, and 1% zinc chloride, the most preferred amount of zinc chloride is concluded to be about 1 part per 100 parts cefuroxime axetil by weight.

What is claimed is:

1. A solid pharmaceutical composition for oral administration comprising cefuroxime axetil as the active ingredient and zinc chloride as a stabilizer.

2. The composition of claim 1, comprising a co-precipitate of cefuroxime axetil, a water soluble diluent, and zinc chloride.

3. The composition of claim 1 or 2 wherein the amount of zinc chloride is from about 0.1 part to about 4 parts per 100 parts cefuroxime axetil by weight.

4. The composition of claim 1 or 2 wherein the amount of zinc chloride is from about 0.2 to about 2 parts per 100 parts cefuroxime axetil by weight.

5. The composition of claim 1 or 2 wherein the amount of zinc chloride is about 1 part per 100 parts cefuroxime axetil by weight.

6. The composition of claim 1 or 2 in the form of a tablet.

7. The composition of claim 1 or 2 in the form of powder or granules for oral suspension.

8. A process of stabilization of cefuroxime axetil in a solid pharmaceutical composition for oral administration comprising the step of adding zinc chloride to the cefuroxime axetil.

9. The process of claim 8, wherein the cefuroxime axetil and zinc chloride are both dissolved in solvent and the solvent is evaporated.

10. The composition of claim 2 wherein the water soluble diluent is sorbitol.

11. The composition of claim 6 wherein the water soluble diluent is sorbitol.

12. The composition of claim 7 wherein the water soluble diluent is sorbitol.

13. A solid pharmaceutical composition comprising a co-precipitate of cefuroxime axetil, a water soluble diluent, and zinc chloride as a stabilizer.

14. The composition of claim 13 wherein the water soluble diluent is sorbitol.

15. The composition of claim 13 or 14 wherein the amount of zinc chloride is from about 0.1 part to about 4 parts per 100 parts cefuroxime axetil by weight.

16. The composition of claim 13 or 14 wherein the amount of zinc chloride is from about 0.2 to about 2 parts per 100 parts cefuroxime axetil by weight.

17. The composition of claim 13 or 14 wherein the amount of zinc chloride is about 1 part per 100 parts cefuroxime axetil by weight.

* * * * *